United States Patent [19]
Wieser

[11] 4,184,092
[45] Jan. 15, 1980

[54] DRIVE CIRCUITS FOR ULTRASONIC TOOTH TREATMENT TRANSDUCERS

[75] Inventor: Alfred Wieser, Bad Homburg, Fed. Rep. of Germany

[73] Assignee: Medtronic GmbH, Fed. Rep. of Germany

[21] Appl. No.: 883,515

[22] Filed: Mar. 6, 1978

[30] Foreign Application Priority Data

Mar. 8, 1977 [DE] Fed. Rep. of Germany ....... 2710049

[51] Int. Cl.$^2$ .......................................... H01L 41/10
[52] U.S. Cl. .................................. 310/316; 318/116
[58] Field of Search ............... 310/314, 316, 317, 318, 310/319, 26; 318/116, 118

[56] References Cited

U.S. PATENT DOCUMENTS

| | | | |
|---|---|---|---|
| 3,085,185 | 4/1963 | Jacke et al. | 310/316 X |
| 3,278,770 | 10/1966 | Shom | 310/316 |
| 3,434,074 | 3/1969 | Libby | 310/316 X |
| 3,586,936 | 6/1971 | McLeroy | 310/316 X |
| 3,668,486 | 6/1972 | Silver | 310/316 X |
| 3,727,112 | 4/1973 | Popescu | 310/316 X |
| 3,819,961 | 6/1974 | Bourgeois et al. | 310/316 |
| 3,989,042 | 11/1976 | Mitsui et al. | 310/319 X |

Primary Examiner—Mark O. Budd
Attorney, Agent, or Firm—Jacobs & Jacobs

[57] ABSTRACT

Ultrasonic tooth treatment apparatus having an electromechanical transducer, such as a magnetostrictive or piezoelectric transducer, and a generator which drives the transducer, with a control signal derived from a change of current and/or frequency occurring upon loading the transducer. This signal disconnects the generator or reduces its power when a predetermined threshold value is exceeded. The generatory may be readjusted to the actual resonant frequency of the transducer. The transducer may be part of the frequency-determining portion of the generator. The generator supplies a pulse-shaped or sinusoidal signal for driving the transducer. A first signal corresponding to the no-load frequency or the no-load current of the transducer is derived. This first signal is compared to a second signal corresponding to the frequency or current of the transducer under load in a sum-or-difference circuit whose output signal forms the control signal and is compared in a comparison circuit to a signal corresponding to the predetermined threshold value.

24 Claims, 3 Drawing Figures

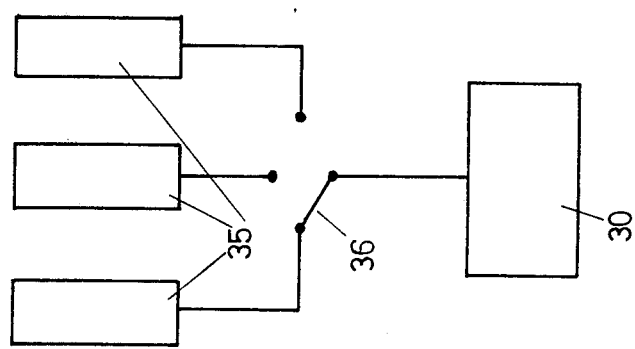
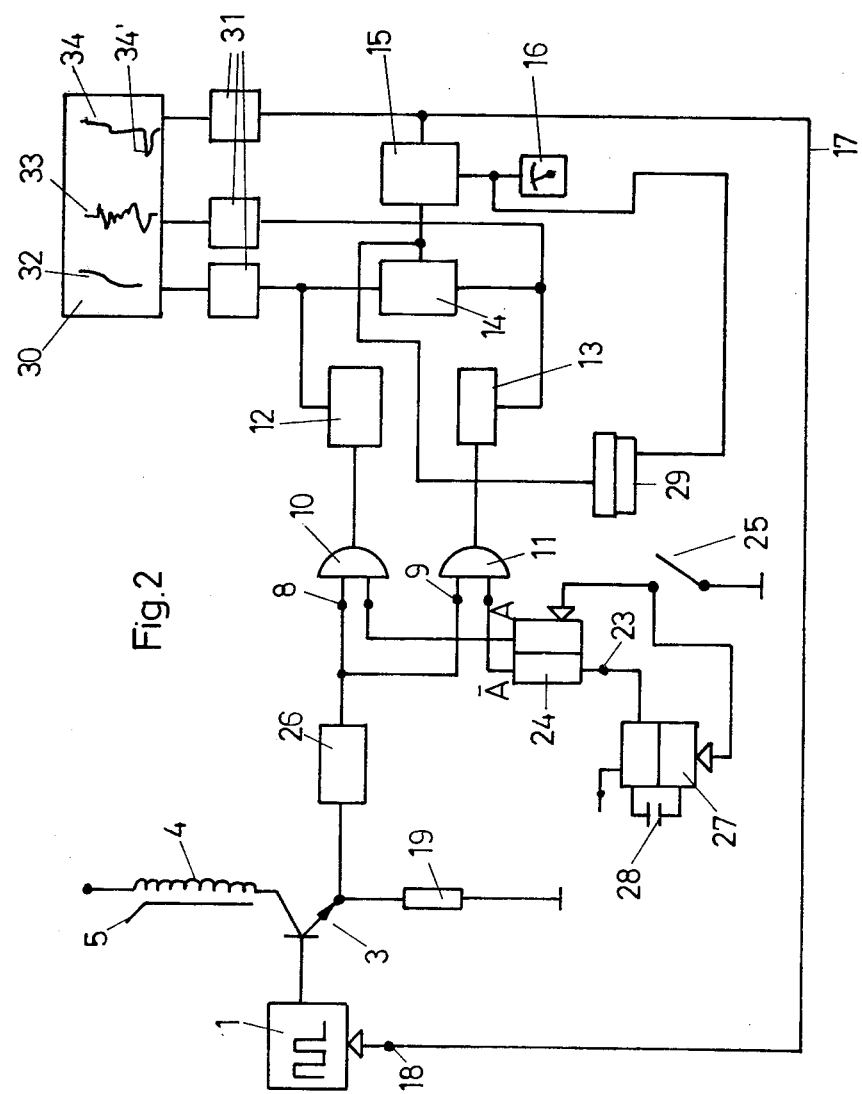

DRIVE CIRCUITS FOR ULTRASONIC TOOTH TREATMENT TRANSDUCERS

The present invention relates to an ultrasonic tooth treatment apparatus having an electromechanical transducer, for instance a magnetostrictive or piezoelectric transducer, and a generator which drives the transducer.

An ultrasonic tooth treatment apparatus of this type has been described, for instance, in West German Provisional Pat. No. 2 459 841.

In this known untrasonic tooth treatment apparatus provision is made for readjusting the pulse oscillator serving as generator to the specific resonant frequency of the transducer, which frequency depends both on the tool used and connected to the transducer as well as on the load on the transducer or the pressure of application with which the tool is pressed against the tooth which is to be treated. By the retuning of the frequency of the generator to the specific actual resonant frequency of the transducer optimum efficiency is to be obtained for the transducer and the ultrasonic tooth treatment apparatus. For the retuning of the oscillator or generator the resonant-circuit characteristic of the transducer is used as criterion.

Since, in ultrasonic tooth treatment apparatus which serve, in particular, for the removal of tartar and the like and are operated with relatively high power the possibility cannot definitely be excluded that if such an instrument is handled improperly, for instance by an operator who is still untrained, and particularly if the tool attached to the transducer is applied too strongly against the tooth to be treated, unintended damage to the tooth or tooth enamel will result, it is desirable in the case of such ultrasonic tooth treatment apparatus to provide means by which a maximum threshold value for this load can be adjusted and which thereupon, when this threshold value is exceeded, automatically disconnect the generator which is driving the transducer or reduce the power of said generator.

It has already been proposed in this connection (Senior patent application No. P2600 877.5) that the generator be shut off by the use exclusively of the characteristic of the resonant circuit of the transducer, which however has the disadvantage that this disconnect or safety function is possibly only when a very specific circuit arrangement is employed. In addition to this, the proposal of said senior unpublished application has the disadvantage that the threshold value at which the generator is turned off or its power reduced depends on the power which has been basically established for the transducer as well as on its resonant frequency and thus also on the tool which is attached to the transducer. Therefore in this older proposal certain difficulties result from the fact that before setting the threshold value at which the generator is to be disconnected, the characteristic of the transducer must be standardized or taken into account, which however is frequently impossible in practical operation.

The object of the present invention is to avoid these drawbacks and to provide an ultrasonic tooth treatment apparatus in which the disconnecting of the generator or the reduction of its power when a predeterminable threshold value for the power produced by the transducer or the pressure of application of the tool against the tooth to be treated is exceeded is independent of the characteristic of the transducer, i.e. in particular also independent of the natural resonance of the transducer, which changes with the use of different tools.

In order to achieve this purpose, an ultrasonic tooth treatment apparatus of the aforementioned type is so developed in accordance with the invention that a control signal is derived from the change in current and/or frequency which occurs when the transducer is subjected to load, said signal disconnecting the generator or reducing its power when a predeterminable threshold value is exceeded.

Since only that change in current and/or frequency which occurs upon the adding of as compared with the unload condition is used as disconnect criterion for the disconnecting in the case of the ultrasonic tooth treatment apparatus of the invention, consideration of the specific transducer characteristic is not necessary for this disconnection, so that different tools can be used with one and the same ultrasonic tooth treatment apparatus or one and the same transducer without further adjustment. In addition to this, it is also possible to use alternately different transducers with a single apparatus. In addition, the setting of the threshold value at which the disconnecting of the apparatus or the reduction of the power of the apparatus takes place is substantially simplified.

In accordance with a further development it is proposed that a first signal be derived which corresponds to the no load frequency of the transducer (4, 5), that this first signal be compared with a second signal corresponding to the frequency of the transducer under load in a sum or difference circuit, and that the output signal of this sum or difference circuit which forms the control signal be compared in a comparison circuit with a signal which corresponds to the predetermined threshold value.

It is furthermore possible for a first signal to be derived corresponding to the no-load current of the transducer, for this first signal to be compared with a second signal corresponding to the current of the transducer under load in a sum or difference circuit, and for the output signal of this sum or difference circuit which forms the control signal to be compared in a comparison circuit with a signal corresponding to the predetermined threshold value.

Further developments of the invention are described in the subordinate claims.

The invention will be described in further detail below with reference to illustrative embodiments shown in the drawing, in which:

FIG. 2 shows the electrical circuit of a second embodiment of the ultrasonic tooth treatment apparatus of the invention;

FIG. 3 shows, in the form of a block diagram, a central recording or monitoring arrangement for a plurality of ultrasonic tooth treatment apparatus in accordance with FIG. 2.

Figure 1:
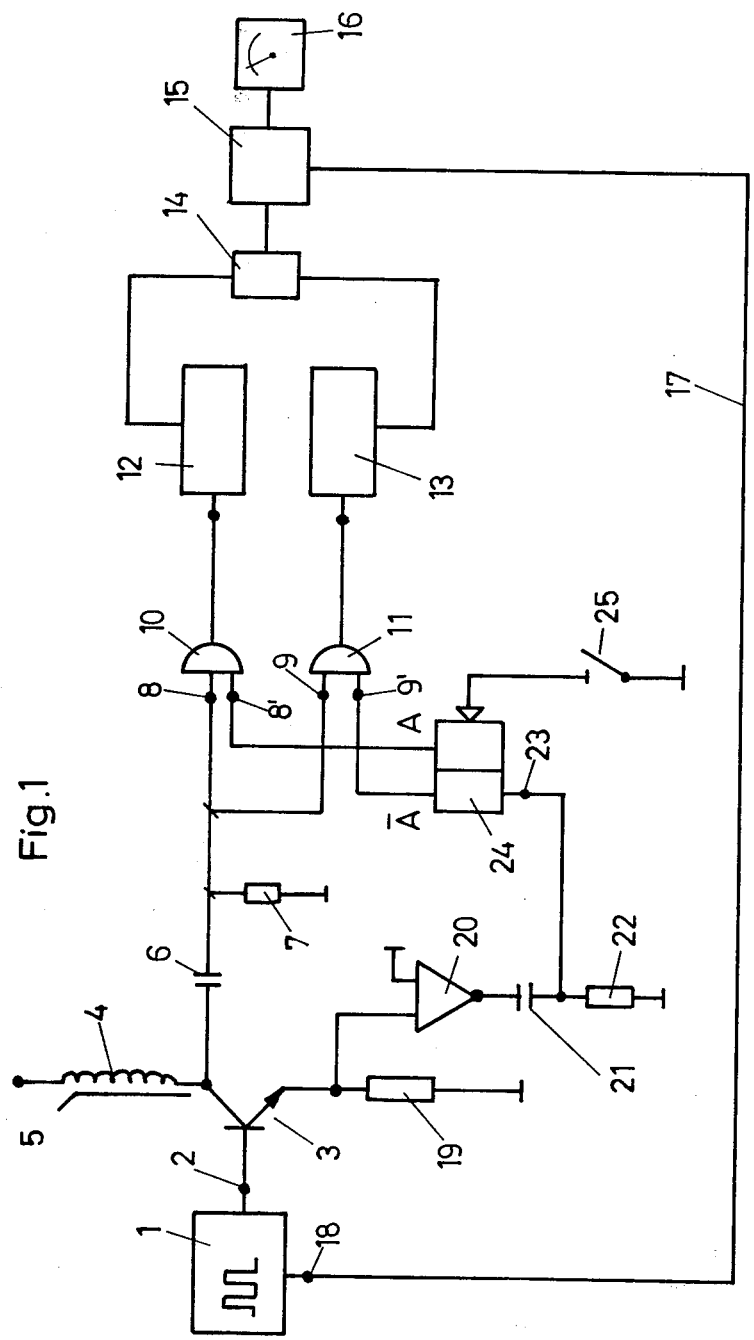
FIG. 1 is the electrical circuit of a first embodiment of the ultrasonic tooth treatment apparatus of the invention.

The ultrasonic tooth treatment apparatus shown in FIG. 1 consists of a generator 1 which, at its output, 2 provides a pulsating or sinusoidal output signal which is fed to the base of a control transistor 3, within the collector circuit of which there is arranged the winding of a magnetostrictive transducer the mechanical output of which bears the tool 5 of the ultrasonic tooth treatment apparatus.

The generator 1 is in this connection provided, for instance, (in a manner not shown in detail) with frequency retuning in such a manner that the frequency of the output signal of the generator is retuned in accordance with the resonant frequency of the transducer, with due consideration of the load at the time, i.e. with consideration of the force with which the tool 5 is being applied against a tooth to be treated, in order in this way to obtain an optimum output.

Furthermore, it is also possible, instead of a magnetostrictive transducer, to use a piezoelectric transducer whose piezo element is then arranged in the collector circuit of the control transistor 3.

To the collector of the control transistor 3 there is furthermore connected a differentiation member consisting of the capacitor 6 and the resistor 7, the one end of the resistor 7 being connected to the ground of the circuit and the capacitor 6 connecting the other end of the resistor 7 to the collector of the control transistor 3. The output signal of the differentiation member which is connected to the junction point between the capacitor 6 and the resistor 7 is fed in each case to an input 8 or 9 of an AND gate 10 or 11 respectively, each AND gate 10 and 11 controlling a memory 12 and 13 respectively. The outputs of these memories are connected to the inputs of a difference-forming logic 14 which supplies an output signal to an input of the comparison circuit 15, to a second input of which the signal of a setting member 16 is fed. The output signal of the comparison circuit 15 is fed, via the line 17, to a control or regulating input 18 of the generator 1 for the readjustment of its power.

In the emitter circuit of the control transistor 3 there is provided a resistor 19 which lies in parallel to the input terminals of an amplifier 20 whose output is connected with a differentiating member consisting of the capacitor 21 and the resistor 22, one end of the resistor 22 being connected with the circuit ground, while the capacitor 21 lies between the other end of the resistor 22 and the output of the amplifier 20. The output signal of the differentiating member which is applied to the junction point between the capacitor 21 and the resistor 22 is fed to the "SET" input 23 of a flip-flop 24 which is so connected that in unset condition, i.e. upon the absence of a signal at the output 23, it has a signal at its output A while on the complementary output $\overline{A}$ there is a "NULL" signal. The outputs A and $\overline{A}$ are connected with the two other inputs 8' and 9' respectively of the AND gates 10 and 11.

The manner of operation of the ultrasonic tooth treatment apparatus shown in FIG. 1 can be described as follows:

Before the apparatus is placed in operation, a threshold value for a maximum hardness or power at which the apparatus will automatically be disconnected is set on the setting member 16, for instance by means of a switch and a scale provided on the switch. The apparatus is now placed in operation, for instance, by connecting the generator 1, the tool 5 provided on the magnetostrictive transducer being not yet in engagement with the tooth to be treated at least immediately upon the turning on of the generator, so that the transducer is operated without load by the generator 1. From the alternating voltage which is present in this connection on the collector of the control transistor 3, a signal is formed by the differentiation member consisting of the capacitor 6 and the resistor 7, this signal corresponding to the no-load frequency of the magnetostrictive transducer and being fed via the AND gate 10 to the memory 12, since upon the connecting of the apparatus the flip-flop 24 is in a condition in which a signal is present on the output A.

If the tool 5 on the magnetostrictive transducer is now brought into contact with a tooth to be treated, the flow of current through the winding and thus also through the resistor 19, changes due to the greater load on the mechanical output of the magnetostrictive transducer, this leading to a change in voltage over this resistor so that a tripping pulse is produced at the output of the differentiating member formed by the capacitor 21 and the resistor 22, i.e. at the junction point between the capacitor 21 and the resistor 20, which pulse switches the flip-flop 24 in such a manner that a signal is now present at the output $\overline{A}$ while the signal at the output A is NULL. This has the result that practically from the start of the first loading of the tool 5 a signal which corresponds to the frequency of the magnetostrictive transducer under load is fed, via the AND gate 11 which is now connected, through from the differentiating member consisting of the capacitor 6 and the resistor 7, to the storage 13 while the storage 12 does not receive any additional signal in view of the fact that the AND gate 10 is blocked.

Since on the one hand the resonant frequency of the transducer shifts towards lower frequencies upon an increase in the load or upon an increase in the pressure of application between the tool 5 and the tooth to be treated and, on the other hand, the generator 1 is so retuned that the frequency of the output signal of the generator corresponds approximately to the instantaneous resonant frequency of the transducer, the signal fed to the storage 13 also differs to a greater or lesser extent, depending on the load, from the signal which has been fed to the storage 12. This difference is established in the difference-forming logic 14 and then compared in the comparison circuit 15 with the value supplied by the adjustment member. As long as the value supplied by the difference-forming logic 14 is below the value which is supplied by the setting member 16 corresponding to the setting effected, that is as long as the load present on the transducer or on the tool 5 is less than the maximum threshold value set on the setting member 16, there is no signal present at the output of the comparison circuit 15. If the value supplied by the setting member 16 is exceeded, however, by the value or signal of the difference-forming logic 14, then the comparison circuit 15 forms an output signal on the line 17, which signal disconnects the generator 1 or reduces the power of said generator.

The above-mentioned retuning of the generator 1 to the instantaneous resonant frequency of the transducer can be effected, for instance, by utilization of the fact that the transducer has the characteristic of an oscillatory circuit whose pass curve shifts as a function of the load on the transducer, so that a change in voltage occurring in this connection on the winding 4 of the transducer or a change in the flow of current through the transducer can be used as readjustment criterion for the generator 1. Such a frequency retuning is described, for instance, in West German Provisional Pat. No. 2 459 841. Of course, it is also possible to use the transducer itself as frequency-determining member for the generator.

After the disconnecting or upon the disconnecting of the tooth treatment apparatus in accordance with FIG. 1, a switch 25 is actuated, which resets the flip-flop, i.e.

places it in a condition in which, once again, a signal is present at the output A while the signal at the output $\overline{A}$ is NULL.

FIG. 2 shows a modified embodiment in which use is made for the safety disconnect of the apparatus exclusively of the fact that the current through the transducer and through the winding 4 is changed, namely reduced or increased upon an increase in the load. The emitter of the control transistor 3 is, in this connection, connected with the input of an analog-digital converter 26 which converts the current which flows through the winding 4 of the transducer and through the control transistor 3, or the average value of said current, into a proportional digital signal which is then fed to the inputs 8 and 9 of the AND gates 10 and 11 respectively. In its basic design the ultrasonic tooth treatment apparatus of FIG. 2 otherwise corresponds to the apparatus of FIG. 1, except, to be sure, that the flip-flop 24 is not switched by a trigger pulse which occurs upon the loading of the transducer but by a time switch 27, for instance a "mono-flop", which, upon the connecting of the apparatus, switches after the charging of a capacitor 28 which serves as time-determining member and thereby supplies a switch pulse to the flip-flop 24.

The manner of operation of the ultrasonic tooth treatment apparatus shown in FIG. 2 can be described as follows:

After the connecting of the apparatus, the generator 1 supplies a control signal to the control transistor 3 which, first of all, operates the magnetostrictive transducer without load. The current which occurs in this connection through the winding 4 leads to a voltage at the resistor 19, which voltage is converted by the analog-digital converter into a digital signal which, corresponding to the position of the flip-flop 24 (a signal is present at the output A), is fed via the AND gate to the memory or the counter 12. After a certain period of time, that is when the capacitor 28 has been charged to a predetermined threshold value, the mono-flop 27 switches and delivers the signal to the SET input 23 of the flip-flop 24 whereby the signal at the output A becomes NULL while a signal is present on the output $\overline{A}$. This, in its turn, has the result that the AND gate 10 is blocked and no further signals can enter the memory or counter 12. All signals thereafter delivered by the analog-digital converter pass via the AND gate 11 to the memory 13, i.e. also those signals which are delivered by the analog-digital converter 26 when the transducer is under load. The switch time of the mono-flop is advisedly selected so short that a switching of the flip-flop 24 in all cases still takes place before the treating dentist has been able to bring the tool 5 of the ultrasonic tooth treatment apparatus into engagement with a tooth which is to be treated.

The difference between the digital signal of the memory 13 which is dependent on the load or on the pressure of application between tool 5 and the tooth to be treated and the no-load signal in the memory 12 is again determined in the difference-forming logic 14 whose output signal is compared in the comparison circuit 15 with a signal supplied by the setting member 16. As soon as the output signal of the difference-forming logic 14 exceeds the signal of the setting member 16, i.e. as soon as the application pressure between the tooth to be treated and the tool 5 has exceeded a predetermined threshold value, the comparison circuit 15 again supplies a signal via the line 17 to the control or regulating input of the generator, as a result of which the generator 1 is disconnected or its power reduced.

In the embodiment shown in FIG. 2, there is furthermore provided a two-part indicating device 29, for instance two LED rows (rows of light-emitting diodes) which are arranged one above the other and light up in different colors in order to show on the one hand the output signal of the difference-forming logic, i.e. the actual application pressure of the tool 5, and on the other hand the signal of the adjustment member 16, i.e. the threshold value set.

Furthermore, in the ultrasonic tooth treatment apparatus of FIG. 2 there is provided a multi-channel recorder 30 whose inputs are connected via digital-analog transducers 31 with the output of the memory 12, the output of the memory 13, and the output of the comparison circuit 15. In this way different parameters are recorded in the recorder 30 in three tracks 32, 33 and 34, namely the no-load load in track 32, the load upon treatment of a tooth plus the no-load load in track 33, and the actual load or application pressure of the tool 5 against the tooth to be treated in track 34, the peak 34' reproducing the release value set or the threshold value set on the setting member 16 at which the automatic disconnect takes place.

The recorder 33 is provided in particular for purposes of training, in order to enable the instructor, based on the recordings of the recorder 30 and on the indication of the indicating device 29 to recognize and judge the course of a dental treatment.

In a large school or training operation the recorder 30 shown in FIG. 3 as well as possibly also the recording device 29 are suitably provided centrally for a plurality of tooth treatment apparatus 35 shown in FIG. 2, the individual ultrasonic tooth treatment apparatus 25 being capable of being connected then alternately to the recorder 30 by means of a selector switch 36.

The invention has been described in detail above with reference to illustrative embodiments. It is self-evident that changes as well as additions are possible without going beyond the inventive concept.

What is claimed is:

1. Ultrasonic tooth treatment apparatus having an electromechanical transducer, a generator operable to drive the transducer, the effective output power of said generator being reducible by a control signal, means for deriving a first signal corresponding to the no-load current through the transducer and for deriving a second signal corresponding to the current through the transducer under load, means for comparing the first and the second signal and for providing a sum or difference output signal from said first and second signal, and means for comparing said output signal with a threshold signal corresponding to a predetermined transducer power and for providing said control signal when said predetermined transducer power is reached.

2. Apparatus according to claim 1 including an analog-digital converter providing said first and said second signal at its output, said means for deriving said first and said second signal comprising a resistor in the emitter circuit of a transistor driving said transducer, voltage of said resistor being applied to the input of said analog-digital converter.

3. Apparatus according to claim 1 including means for indicating said control signal.

4. Apparatus according to claim 1 including means for indicating the predetermined transducer power.

5. Apparatus according to claim 1, including means for readjusting the frequency of said generator to the actual resonant frequency of the transducer.

6. Apparatus according to claim 1, including a transducer as part of the frequency-determining member of the generator.

7. Apparatus according to claim 1, wherein the supply voltage of the generator is controlled by said control signal.

8. Ultrasonic tooth treatment apparatus having an electromechanical transducer, a generator operable to drive the transducer, the effective output power of said generator being reducible by a control signal, means for deriving a first signal corresponding to the no-load frequency of the transducer and for deriving a second signal corresponding to the frequency of the transducer under load, means for comparing the first and the second signal and for providing a sum or difference output signal from said first and second signal, and means for comparing said output signal with a threshold signal corresponding to a predetermined value of transducer power and for providing said control signal when said predetermined transducer power is reached.

9. Apparatus according to claim 8, further comprising electronic switching means operable to selectively connect said means for deriving the first and the second signal with a first channel having a first memory and with a second channel, the outputs of the first and the second channel being connected with said means for comparing the first and the second signal, said switching means being so controlled that the first signal is fed to the first channel upon no-load condition of the transducer and that the second signal is fed to the second channel upon load condition of the transducer.

10. Apparatus according to claim 9, including a second memory in said second channel.

11. Apparatus according to claim 9, including means for generating a switch signal for switching said switching means.

12. Apparatus according to claim 11, wherein said switch signal is derived from a change in current through the transducer, when the transducer is placed under load.

13. Apparatus according to claim 11, wherein said means for providing said switch signal is a time-delayed switch having a predetermined delay time and being placed in operation upon switching on the apparatus.

14. Apparatus according to claim 12, wherein said means for providing said switch signal include a resistor positioned in the emitter circuit of a transistor driving said transducer, and differentiation means generating said switch signal from a change in voltage across said resistor.

15. Apparatus according to claim 9, wherein said electronic switching means comprises two AND gates, one gate being in the first channel and the other gate being in the second channel, one input of each gate being connected with the input of said circuit while second inputs of each gate are controlled in push-pull corresponding to said switch signal.

16. Apparatus according to claim 15 including a flip-flop driven by said switch signal, second inputs of said AND gates being each connected with one of two complementary outputs of said flip-flop.

17. Apparatus according to claim 8 including means for indicating said control signal.

18. Apparatus according to claim 8 including means for indicating the predetermined transducer power.

19. Apparatus according to claim 9, including means for displaying the output signal of said first and said second channel.

20. Apparatus according to claim 8 including means for displaying the control signal reducing generator power.

21. Apparatus according to claim 8 including means for readjusting the frequency of said generator to the actual resonant frequency of the transducer.

22. Apparatus according to claim 8 including a transducer as part of the frequency-determining member of the generator.

23. Apparatus according to claim 8, wherein the supply voltage of the generator is controlled by said control signal.

24. Apparatus according to claim 9, including means for displaying the control signal reducing generator power.

* * * * *